United States Patent [19]

Claude et al.

[11] Patent Number: 5,510,508

[45] Date of Patent: Apr. 23, 1996

[54] METHOD OF PREPARING A COMPOUND DERIVED FROM ASPARTAME, USEFUL AS A SWEETENING AGENT

[76] Inventors: Nofre Claude, 119 Cours Albert Thomas, 69003 Lyons; Jean-Marie Tinti, 5, Impasse de la Drelatière, 69680 Chassieu, both of France

[21] Appl. No.: 436,576

[22] Filed: May 8, 1995

[30] Foreign Application Priority Data

May 9, 1994 [FR] France .................. 94 05674

[51] Int. Cl.$^6$ ............................... C07C 229/36
[52] U.S. Cl. ................................................ 560/41
[58] Field of Search .................................. 560/41

[56] References Cited

U.S. PATENT DOCUMENTS

| 4,645,678 | 2/1987 | Nofre et al. | 426/548 |
| 4,935,517 | 6/1990 | Nofre et al. | 544/322 |

FOREIGN PATENT DOCUMENTS

WO94/11391  5/1994  WIPO.

OTHER PUBLICATIONS

Ohfune et al., *Chemistry Letters*, pp. 441–444 (1984).
CA115: 247455x (1991).

*Primary Examiner*—José G. Dees
*Assistant Examiner*—Barbara S. Frazier
*Attorney, Agent, or Firm*—Armstrong, Westerman, Hattori, McLeland & Naughton

[57] ABSTRACT

A method of preparing N-[N-(3,3-dimethylbutyl)-L-α-aspartyl]-L-phenylalanine 1-methyl ester of the formula

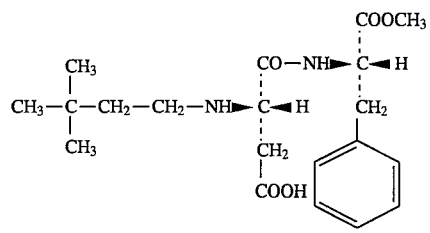

useful as a sweetening agent, wherein an aqueous-alcoholic solution of aspartame and 3,3-dimethylbutyraldehyde of pH 4.5–5 is treated, at room temperature, with hydrogen at a pressure less than or equal to 1 bar, in the presence of a catalyst selected from the group comprising platinum or palladium on activated carbon or in the form of platinum or palladium black, and wherein the product formed is purified by precipitation and filtration after removal of the alcohol part of the solvent under vacuum.

8 Claims, No Drawings

METHOD OF PREPARING A COMPOUND DERIVED FROM ASPARTAME, USEFUL AS A SWEETENING AGENT

The present invention relates to an improved method of preparing a compound derived from aspartame, useful as a sweetening agent.

More precisely, the present invention relates to a method of preparing an N-substituted derivative of aspartame, namely N-[N-(3,3-dimethylbutyl)-L-α-aspartyl]-L-phenylalanine1-methyl ester of the formula

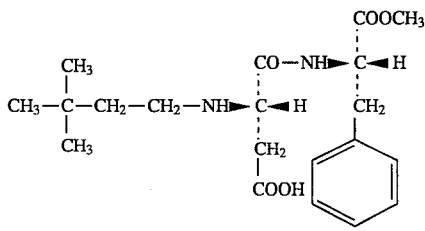

This compound constitutes a very potent sweetening agent since its sweetening potency, on a weight basis, is at least 50 (fifty) times that of aspartame and about 10,000 (ten thousand) times that of sucrose (table sugar).

As sweetening agents are mainly intended for human consumption in foods, they have to be prepared by methods which make it possible to obtain high-purity products practically free of contaminants or degradation products.

Moreover, to be usable on the industrial scale, these methods must be mastered to perfection so as to be reproducible and of relatively low cost.

Insofar as the compound whose method of preparation forms the subject of the present invention is an aspartame derivative, it seems advantageous to look for a synthetic route which uses aspartame as the starting material or intermediate.

As aspartame is in fact the most widely used synthetic sweetening agent at the present time, it meets the standards required for use in foods; furthermore, its industrial preparation has been mastered to perfection at relatively low cost, despite its dipeptide structure.

However, it is known that it is relatively difficult to use aspartame as the starting material or intermediate in an industrial synthesis.

Aspartame in fact has a relatively low solubility in the majority of organic solvents, generally being less than a few grams per liter.

Furthermore, although the solubility of aspartame is higher in aqueous media, its stability is relatively low in these media.

Moreover, any attempt to raise the temperature in order to improve the solubility of aspartame worsens its degradation processes.

Under these conditions, the object of the present invention is to solve the technical problem which consists in providing an improved method of preparing the abovementioned aspartame derivative, which can be carried out easily and reproducibly on the industrial scale at a relatively low cost price, and which uses aspartame as the starting material or intermediate.

It has been discovered, and it is this which constitutes the basis of the present invention, that it is possible to obtain the abovementioned N-alkylated aspartame derivative directly from aspartame in a single step with an extremely high yield and a very high purity compatible with the use of this compound in the food sector.

According to the present invention, the method of preparing N-[N-(3,3-dimethylbutyl)-L-α-aspartyl]-L-phenylalanine1-methyl ester of the formula

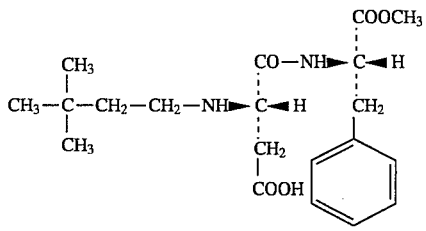

comprises treating a solution of aspartame and 3,3-dimethylbutyraldehyde, at room temperature, with hydrogen at a pressure less than or equal to 1 bar (0.1MPa), in the presence of a catalyst based on platinum or palladium.

In an advantageous embodiment of the invention, the abovementioned catalyst is selected from the group comprising platinum on activated carbon, palladium on activated carbon, platinum black and palladium black.

In a particularly advantageous embodiment, the hydrogenation is carried out in the presence of 5% platinum on activated carbon at a relative pressure of 1 bar, or in the presence of 10% palladium on activated carbon at atmospheric pressure or at a relative pressure of 1 bar.

In a currently preferred exploitation of the invention, the solution of aspartame and 3,3-dimethylbutyraldehyde is an aqueous-alcoholic solution of pH 4.5–5 obtained by mixing a 0.1M solution of acetic acid and methanol, the concentration of aspartame in this solution being between 50 and 60 g/l and that of 3,3-dimethylbutyraldehyde being between 20 and 30 g/l.

According to an advantageous feature of the invention, the product formed is purified by precipitation and filtration after removal of the alcohol part of the solvent under vacuum.

Thus, by the reductive N-alkylation of aspartame, the method according to the invention makes it possible to obtain a very pure sweetening compound with a very high yield.

Numerous examples of reductive N-alkylation using hydrogen associated with catalysts are described in the literature (see, for example, the review by P. N. Rylander, "Catalytic Hydrogenation in Organic Syntheses", Academic Press, San Diego, 1993, pp. 165–174). However, it has only been possible to apply this general technique to the method described in the present invention by selecting the catalysts and by adopting very specific experimental conditions which alone have resulted in the high analytical purity necessary for the use of the compound forming the subject of the method of the present invention in foods.

It has in fact been found that the quality of the desired product depends very closely on the experimental conditions applied during the implementation of the method. The nature of the catalyst, and to a lesser extent the hydrogenation time and pressure and the nature and pH of the reaction medium, have thus proved to be essential parameters.

It should be noted that in the case of hydrogenation reactions on the industrial scale, conditions which afford an appreciable reduction in the reaction time to the order of a few hours, while at the same time preserving a satisfactory yield and remaining within pressure ranges below or equal to 1 bar (0.1 MPa), are very sought after. Although generally accelerating the reaction, the use of high pressures is not normally desirable for reasons of safety and equipment cost.

The hydrogenation catalysts used within the framework of the present invention act unexpectedly, on the one hand at relative pressures less than or equal to 1 bar (0.1MPa) and on the other hand in times less than or equal to 24 hours.

Monitoring of the progress of the reaction by sampling and evaluation of the product formed by high performance liquid chromatography (HPLC) enables those skilled in the art easily to determine the hydrogenation time most appropriate to the conditions used.

Among the possible catalysts, those based on platinum or palladium dispersed on activated carbon or in the form of platinum or palladium black have proved particularly advantageous.

It has been observed that the compound of the invention can also be prepared with other catalysts, such as nickel on silica (Aldrich no. 20,878–7), nickel on silica and alumina (Aldrich no. 20,877–9), Raney nickel (Aldrich no. 22,167–8), ruthenium black (Aldrich no. 32,671–2), ruthenium on carbon (Aldrich no. 28,147–6), palladium hydroxide on carbon (Aldrich no. 21,291–1), palladium oxide (Aldrich no. 20,397–1), rhodium black (Aldrich no. 26,734–1), rhodium on carbon (Aldrich no. 33,017–5) or rhodium on alumina (Fluka no. 83720). However, these catalysts have been found either to be less active necessitating higher hydrogen pressures in particular, or to be less selective, resulting especially in the reduction of the aromatic ring carried by the aspartame or by the desired N-alkylated derivative thereof.

It has also been observed that higher hydrogenation pressures or longer hydrogenation times than those used in the method of the invention can also affect the yield and quality of the finished product. The same applies to the amounts of catalyst used, which also have an appreciable influence on the hydrogenation times.

The catalysts selected within the framework of the present invention have proved particularly effective at concentrations of between 5 and 20%, based on the aspartame.

The aqueous-alcoholic solution of pH 4.5–5 used in the method of the invention has proved particularly advantageous by permitting rapid dissolution of the reactants and by favoring the separation of the desired product in a state of high purity during the treatment. The use of a wholly aqueous reaction medium actually causes the product to precipitate and to aggregate with the catalyst. The reaction times are then longer and the catalyst is difficult to separate off.

It has also been found that a pH of around 4.5–5 for the reaction medium accelerates the reaction while at the same time substantially reducing the aspartame degradation processes.

In summary, choosing very specific catalysts which work under low hydrogen pressures, often in a very short time, at room temperature and in an aqueous-alcoholic medium of pH 4.5–5 makes it possible to observe the stability and solubility constraints associated with aspartame. The high crude yields obtained under these conditions make it easier to obtain a product of very high quality, which furthermore is easily recovered by simple precipitation after removal of the alcohol part of the reaction solvent.

The present invention will be described more completely with the aid of the following Examples, which must not be considered as limiting the invention.

EXAMPLE 1

The following are introduced successively, with stirring, into a reactor equipped with a stirrer capable of ensuring a very good transfer of gaseous hydrogen into the liquid phase: 60 cm$^3$ of a 0.1M aqueous solution of acetic acid, 1 g of 5% platinum on activated carbon (Aldrich product no. 33,015–9), 2.55 g of 3,3-dimethylbutyraldehyde, 30 cm$^3$ of methanol and 5 g of aspartame.

After the reactor has been purged with a stream of nitrogen, the mixture is hydrogenated at a relative pressure of 1 bar (0.1MPa) and at room temperature. The progress of the reaction is monitored by taking a crude sample and assaying the product formed by high performance liquid chromatography (HPLC). The concentration of desired product is determined by comparison with a calibration curve established beforehand. After a hydrogenation time of 2 hours, the formation of 100% of the expected product is observed.

The reaction is then interrupted by purging the reactor with a stream of nitrogen and filtering the catalyst off on a fine filter (0.5 μm). If necessary the filtrate is adjusted to pH 5 by the addition of a few drops of a 1N solution of sodium hydroxide. The methanol is then removed by evaporation under vacuum, the temperature being kept below 40° C. A white solid rapidly precipitates. The mixture is stirred for a few hours more at room temperature in order to complete the precipitation. The product is filtered off, dried and washed with about 50 cm$^3$ of hexane. 4.4 g of N-[N(3,3-dimethylbutyl)-L-α-aspartyl] -L-phenylalanine 1methyl ester (yield 69%) are finally obtained in the form of a white powder of high purity (greater than 98% by HPLC).

EXAMPLE 2

With the same equipment, the same solvent and the same reactants at the same concentrations as those described in Example 1, but using 1 g of 10% palladium on activated carbon (Fluka product no. 75990) as the catalyst, the hydrogenation being carried out at a relative pressure of 1 bar (0.1MPa), again at room temperature, the reaction is stopped after 2 hours (96% of product formed). After purification by precipitation according to the protocol described in Example 1, 4.3 g of the expected product (yield 68%) are obtained in the form of a white powder of very high purity (greater than 98% by HPLC).

EXAMPLE 3

With the same equipment, the same solvent and the same reactants at the same concentrations as those described in Example 1, but using 1 g of 10% palladium on activated carbon (Fluka product no. 75990) as the catalyst, the hydrogenation being carried out at atmospheric pressure, again at room temperature, the reaction is stopped after 24 hours (97% of product formed). After purification by precipitation according to the protocol described in Example 1, 4.3 g of the expected product (yield 68%) are obtained in the form of a white powder of very high purity (greater than 98% by HPLC).

EXAMPLE 4

With the same equipment, the same solvent and the same reactants at the same concentrations as those described in Example 1, but using 1 g of platinum black (Aldrich product no. 20,591–5) as the catalyst, the hydrogenation being carried out at atmospheric pressure, again at room temperature, the reaction is stopped after 1 hour (96% of product formed). After purification by precipitation according to the protocol described in Example 1, 4.4 g of the expected product (yield 69%) are obtained in the form of a white powder of very high purity (greater than 98% by HPLC).

EXAMPLE 5

With the same equipment, the same solvent and the same reactants at the same concentrations as those described in Example 1, but using 1 g of palladium black (Aldrich product no. 20,583-4) as the catalyst, the hydrogenation being carried out at atmospheric pressure, again at room temperature, the reaction is stopped after 16 hours (98% of product formed). After purification by precipitation according to the protocol described in Example 1, 4.4 g of the expected product (yield 69%) are obtained in the form of a white powder of very high purity (greater than 98% by HPLC).

The purity of the compound prepared by the method of the invention is checked by the conventional techniques of thin layer chromatography, infrared spectrometry, ultraviolet spectrometry, high performance liquid chromatography (HPLC), thermal analysis, optical rotation, nuclear magnetic resonance and percentage analysis.

The physical criteria obtained for the compound prepared according to the invention are given below. Amorphous, odorless, non-hygroscopic white powder.

Molecular formula: $C_{20}H_{30}N_2O_5$.

Molecular weight: 378.4.

Water content (Karl Fischer method): 3 to 6%.

Thin layer chromatography: 60 F254 silica gel on aluminum sheets (Merck no. 5554), eluent: butanol/acetic acid/water (8:2:2), developing with ninhydrin, Rf: 0.54.

Infrared spectrum (KBr) $cm^{-1}$: 3587 (HOH), 3444, 3319 (NH), 3028 (CH), 2957, 2867 (CH), 1733 ($COOCH_3$), 1690 (CONH), 1594 ($COO^{31}$), 1565, 1541, 1440, 1414, 1390, 1368, 1278, 1245, 1218, 1173, 1119, 999, 758, 701 (CH). Ultraviolet spectrum: maxima at 214 nm and 257 nm. High performance liquid chromatography on a Merck column of the type "Lichrospher 100 RP-18 endcapped", length 244 mm, diameter 4 mm, eluent: 65 mM ammonium acetate/acetonitrile (65:35), flow rate: 1 ml/min, detector: refractometer, retention time: 7.7 min. Differential thermal analysis from 40 to 350° C. at 10° C./ min: melting point: 84° C., no decomposition below 200° C. Optical rotation: $[\alpha]_D^{20}$ =−46.5°±1.5 (C=2, methanol).

Nuclear magnetic resonance spectrum (H, 200MHz, DMSO-$d_6$): 0.81 (s, 9H), 1.28 (m, 2H), 2.38 (m, 4H), 2.9 (m, 2H), 3.44 (m, 1H), 3.62 (s, 3H), 4.55 (m, 1H), 7.22 (m, 5H), 8.54 (d, 1H).

Percentage analysis: found (theory for 4.5% of water): C 60.51 (60.73), H 7.86 (8.12), N 7.07 (7.08), O 23.62 (24.04).

The compound prepared by the method which has now been described and illustrated is particularly useful for sweetening a variety of products, in particular drinks, foods, confectionery, pastries, chewing gums, hygiene products and toiletries, as well as cosmetic, pharmaceutical and veterinary products.

What is claimed is:

1. A method of preparing N-[N-(3,3-dimethylbutyl)-L-α-aspartyl]-L-phenylalanine 1-methyl ester of the formula

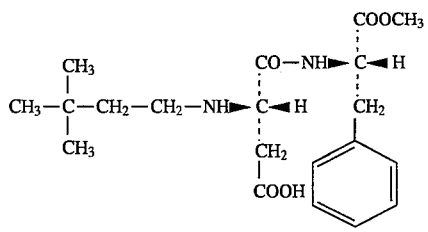

which comprises treating a solution of aspartame and 3,3-dimethylbutyraldehyde, at room temperature, with hydrogen at a relative pressure equal to or less than 1 bar (0.1MPa), in the presence of a catalyst based on platinum or palladium.

2. A method according to claim 1 wherein the catalyst is selected from the group consisting of platinum on activated carbon, palladium on activated carbon, platinum black and palladium black.

3. A method according to claim 1 wherein the hydrogenation is carried out in the presence of 5% platinum on activated carbon at a relative pressure of 1 bar.

4. A method according to claim 1 wherein the hydrogenation is carried out in the presence of 10% palladium on activated carbon at a relative pressure of 1 bar or at atmospheric pressure.

5. A method according to claim 1 wherein the hydrogenation is carried out in the presence of platinum black or palladium black at atmospheric pressure.

6. A method according to claim 1 wherein the solution of aspartame and 3,3-dimethylbutyraldehyde is an aqueous-alcoholic solution of pH 4.4–5 obtained by mixing a 0.1M solution of acetic acid and methanol.

7. A method according to claim 1 wherein the concentration of aspartame in the aqueous-alcoholic solvent is between 50 and 60 g/l and the concentration of 3,3-dimethylbutyraldehyde is between 20 and 30 g/l.

8. A method according to claim 1 wherein the product formed is purified by precipitation and filtration after removal of the alcohol part of the solvent under vacuum.

* * * * *